(12) United States Patent
Sugiyama et al.

(10) Patent No.: US 6,331,712 B1
(45) Date of Patent: Dec. 18, 2001

(54) SECTION FORMATION OBSERVING METHOD

(75) Inventors: Yasuhiko Sugiyama; Toshiaki Fujii, both of Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/271,805

(22) Filed: Mar. 18, 1999

(30) Foreign Application Priority Data

Mar. 19, 1998 (JP) .................................................. 10-070994

(51) Int. Cl.⁷ .................................. G21G 5/00; G21K 5/10
(52) U.S. Cl. ...................... 250/492.21; 250/310; 250/307
(58) Field of Search .................................... 250/307, 306, 250/310, 492.2

(56) References Cited

U.S. PATENT DOCUMENTS 5,401,972 * 3/1995 Talbot et al. ........................ 250/491.1

OTHER PUBLICATIONS

"Dynamic Threshold–Voltage MOSFET (DTMOS) for Ultra–low voltage operation", F.Assaderaghi, D. Sinitsky, S.A.Parke, J. Bokor, P.K. Ko, and C. Hu, IEDM Tech. Dig., 33.1.1, 1994.*

* cited by examiner

*Primary Examiner*—Jack Berman
*Assistant Examiner*—Kalimah Fernandez
(74) *Attorney, Agent, or Firm*—Adams & Wilks

(57) ABSTRACT

A focused ion beam apparatus having an ion source, a focusing optical system and a scanning electrode scans the focused ion beam across a desired region of a sample surface to form a cross-section in which stacked conductors separated by an insulating film are exposed. To prevent charge-up of the sample due to an electrically floating nature of a conductor, a thin hole is formed using the focused ion beam to extend from one conductor to another. Etched particles are adhered to a side surface of the hole due to thin hole formation, with the result that a conductive film is formed electrically connecting the conductors. A floating conductive film is put into contact with a non-floating film to thereby avoid charge-up during observation of the sample with a charged particle beam. A secondary charged particle detector detects secondary charged particles generated in response to ion beam irradiation and outputs a corresponding signal, and a display unit displays an image of the sample based on the output signal of the secondary charged particle detector.

20 Claims, 4 Drawing Sheets

SECTION FORMATION OBSERVING METHOD

BACKGROUND OF THE INVENTION

The present invention relates to a method for forming a section of a sample, such as a semiconductor integrated circuit and ceramics substrate, having a plurality of conductive layers by using a focused ion beam to observe the section.

There is known, as a method to form and observe a section for observing a fine structure of a sample, a method of repeatedly irradiating a focused ion beam to a region having as a side a section observation position of a sample to form a recess (hole) in the sample as disclosed for example in JP-A-2-123749 so that a section of the sample appeared in a sidewall of the recess is observed by scanning and irradiating another charged particular beam.

FIGS. 1A and 1B show, as an example of a sample including a plurality of conductive layers, an interconnect leading to a gate of a MOSFET. Explanation will be made on a method to observe a section obtained by cutting the interconnect.

FIG. 1A is a plan view of a gate interconnect 51 portion. A source region 52 and a drain region 53 are formed on both sides of the gate interconnect 51 in a surface portion of a substrate 50. The source interconnect 55 and the drain interconnect 56 are respectively connected to the source region 52 and the drain region 53 through contacts 54. Explanation is made for a case that the gate interconnect 51 is observed, from a direction of an arrow C, in a section at a position (broken line A–B) between the source region 52 and the drain region 53. A work frame 60 (hole) is defined as in FIG. 1A, which is a region where a focused ion beam is irradiated to form a recess. Subsequently, a focused ion beam is scanned within the work frame 60 to open a hole. As a result, a recess 61 is formed as shown in FIG. 1B. The section of the gate interconnect 51 can be observed by observing in a direction of an arrow D shown in FIG. 1B.

At this time, the gate interconnect 51 (on a D side) leading to the MOSFET gate is separated from the conductive layers, such as other interconnects and semiconductor substrate, by the section formation, and is thus rendered in an electrically floating state. Because the floating-state gate interconnect 51 leading to the gate is formed on a substrate 50 surface through a gate oxide film 57, they form a capacitor. In this state, if charged particles, such as a focused ion beam or electron beam, are irradiated for observation, the charges are charged in the capacitor thus formed. A so-called charge-up phenomenon occurs wherein the potential of the floating gate interconnect 51 increases with respect to a potential of the substrate 50 when irradiating a focused ion beam, and decreases in the case of an electron beam. That is, a problem occurs because of the charge-up phenomenon when the section is observed by irradiating with a focused ion beam or electron beam in a D direction.

In particular, generally in the case of an ion beam the effected charge-up is prominent. That is, in the case of a focused ion beam, the secondary electrons are withdrawn in the section due to charge-up in the observation surface (interconnect section) to a positive potential. This makes it impossible to detect sufficient secondary electrons for obtaining an image. As a result, there is a problem in that the interconnect rendered in charge-up for the image is dark and observation is impossible.

As a countermeasure to this, there is a method disclosed for example in JP-A-7-45681 that the conductive layer in electrically floating is formed with a section separately from one for observation, an exposed new section is irradiated by a focused ion beam while blowing a metal compound gas thereby forming a metal film, and the conductive layer in floating is electrically connected to a sample substrate to avoid a charge-up. This method is effective as a means to avoid a charge-up phenomenon. However, there have been such problems that a metal compound gas blowing mechanism is required besides the focused ion beam irradiation system, and there is necessity of operations of second section formation and the succeeding metal film formation.

Meanwhile, in recent years line widths have become narrow and the gate oxide film formed between the substrate 50 and the gate interconnect 51 has become thin. In particular, the area of the floating conductive layer has been decreased by section formation due to refining in a forming region. Due to this, there has been a drastic decrease in capacitance of a capacitor formed in the process of section formation, and there has been increase in relative potential difference of the gate to the substrate due to floating phenomenon. As stated before, because the decrease in gate oxide film thickness results in a lower withstand voltage, the possibility of sample damage due to charge-up is increased. In particular, before forming a floating conductive layer in the process of section formation, the electric charges due to focused ion beam irradiating are discharged through the conductive layer. The section is observed by irradiating a scanning focused ion beam or scanning electron beam to the formed section and detecting secondary charged particles occurring from the section. However, after a recess 61 for section observation is formed and the conductive layer is rendered in a floating state, electric charges are accumulated in the floating conductive layer during formation of a portion lower than the conductive layer, causing a charge up phenomenon. There is a problem in that a high voltage is applied to the thin gate oxide film that is low in withstand voltage, resulting in damage to the sample as the case may be.

SUMMARY OF THE INVENTION

The present invention has an object to solve these problems.

That is, in order to avoid the problem due to the floating conductive film, a second conductivity layer region formed in a electrically floating state by the section forming process is electrically connected to another non-floating first conductivity layer region (substrate). At this time, realization is made by continuously irradiating a focused ion beam to one point without scanning, or otherwise irradiating it with scanning over an extremely narrower region than the recess formed for section observation.

That is, the present invention is a sample section formation observing method, in a sample including a second conductive layer overlying a first conductive layer through an insulating layer, characterized by comprising: a first process of irradiating a focused ion beam repeatedly scanning at a predetermined region of the sample and forming a recess to form a sidewall in which the second conductive layer and at lease the first conductive layer are exposed, a second process of irradiating the focused ion beam at a region other than the predetermined region from above the second conductive layer rendered in an electrically floating state by the first process to provide a hole reaching the first conductive layer thereby electrically connecting between the first conductive layer and the second conductive layer, and a third process of observing a desired exposed portion in the recess using a charged particle beam.

Although scan irradiation is best effective at a site where the second conductive layer in a floating state is overlapped with the first conductive region positioned thereunder through the insulating film, it is possible to realize the effect of the desired object if an electrical connection is realized between the two electrically independent conductive regions, by a resistance with a sufficient degree for discharging charges that typically are a cause of charge-up.

FIGS. 2A–2B show section of a hole 62 formed by scanning/irradiating a focused ion beam. In the case where the recess formed as in FIG. 2A is shallow in depth (where the hole is opened shallower in depth than a broadest diameter), the substance sputter-etched is discharged from the hole by irradiating focused ion beam ions 71. However, where the recess formed as in FIG. 2B is deep in depth (where the hole is opened deeper in depth than a broadest diameter) due to the proceeding of sputter etch forming, the formed portion by the focused ion beam is at a deep portion in the hole 62. Accordingly, the discharge speed of the etched substance cannot catch up with the etch speed, and the difference deposited substance 72 adheres to the section thereby making it impossible to form the hole to a depth proportional to forming time. Furthermore, as shown in FIG. 2C, the re-deposited substance 72 left at a deep portion of the hole 62 is stirred by the ion beam into a conductive substance mixed state. As a result, a conductive region can be formed at a side surface. That is, the first conductive layer and the second conductive layer are placed in conduction.

When section observation is carried out by a charged particle beam, electric charges are discharged through a newly formed electric path. As a result, charge-up does not occur and a clear interconnect section can be observed.

DETAILED DESCRIPTION OF THE INVENTION

Figure 3:
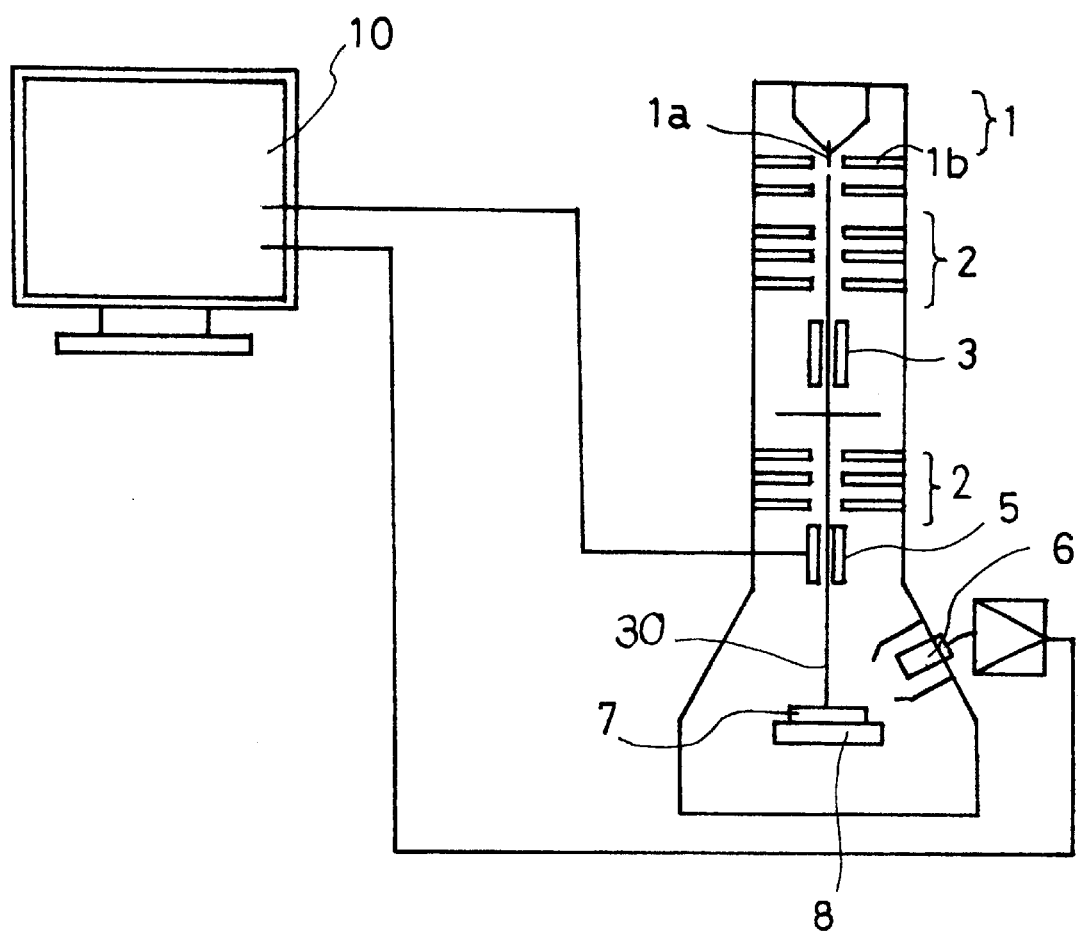
FIG. 3 is a sectional view of an apparatus for carrying out the present invention.

The device for carrying out the present invention will be shown in FIG. 3. A liquid metal ion source 1 has a needle 1a to generate an ion beam by an electric field caused by a leading electrode 1b. The ion beam thus taken out is focused by an ion beam optical system comprising an electrostatic lens 2 and the like, being formed into a focused ion beam 30. A beam blanking electrode 3 and a deflection electrode 5 are provided on an ion beam optical axis. The beam blanking electrode 3 turns on and off the irradiation of the focused ion beam 30 onto a sample 7. The deflection electrode 5 controls irradiation position of the focused ion beam 30. By inputting scanning signals to the deflection electrode 5, the focused ion beam 30 can be scanned over and irradiated to an arbitrary region on the sample 7.

The sample 7 is placed on a sample stage 8 which is movable at least in three axes of X, Y, Z and can tilt and rotate the sample. In the vicinity of a focused ion beam 30 irradiation position of the sample 7, is provided a secondary charged particle detector 6 for detecting secondary charged particles occurring from the sample 7 due to irradiation of the focused ion beam. The state of a surface of the sample 7 is displayed on a display CRT 10 based on the intensity of secondary charged particles detected by the secondary charged particle detector 6.

Figure 1A:
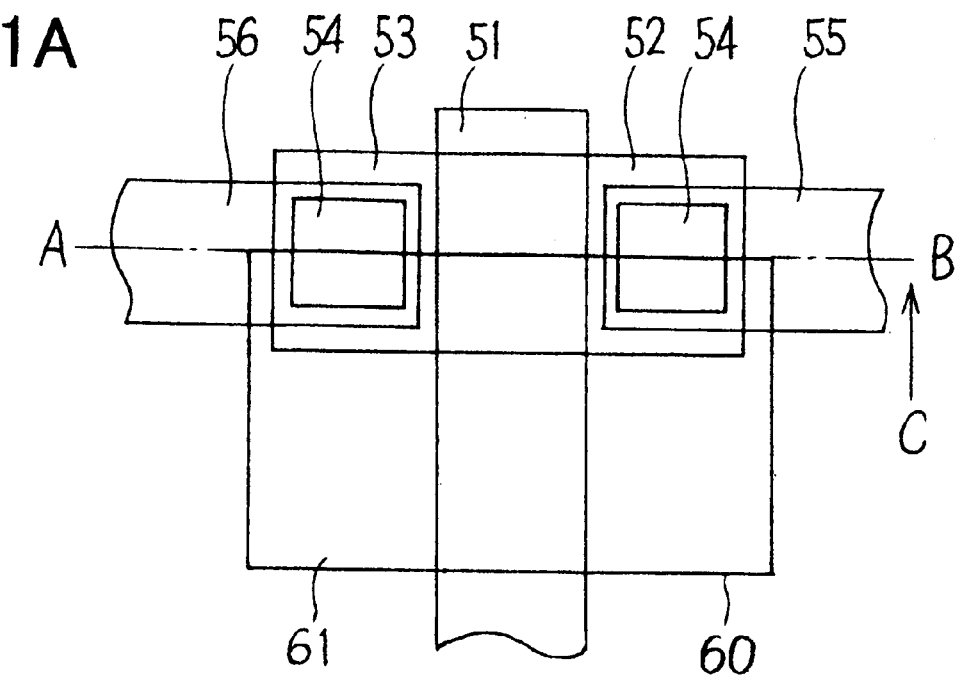
FIG. 1A is a sample plan view and FIG. 1B is a perspective view.
Figure 1B:
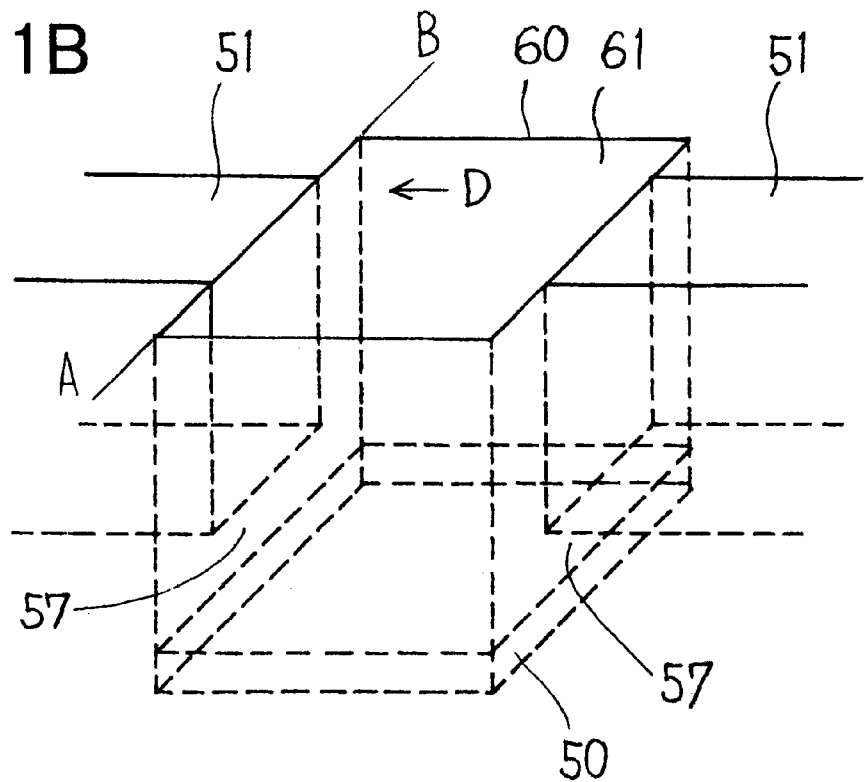

Next, a method of the present invention will be explained. The beam blanking electrode 3 is kept on. The sample has, as was shown in FIG. 1A and FIG. 1b, a substrate 50 as a first conducting layer and a gate interconnect 51 formed thereon as a second conducting layer through an insulating layer 57. The sample 7 is rested on the sample stage 8. Subsequently, a not-shown sample chamber (sub-chamber) in which the sample stage 8 is provided is evacuated by a not-shown vacuum pump. Then the sample stage 8 is moved to a main chamber by passing through a not-shown sub-gate. Further, movement is made such that a predetermined position of the sample 7 comes onto the optical axis and focus of the focused ion beam. The beam blanking electrode 3 is turned off to irradiate the focused ion beam 30 onto the sample 7. At this time, the focused ion beam 30 is scanned and irradiated by the deflection electrode 5 with using a work frame 60 as shown in FIG. 1A. Simultaneously, secondary charged particles occurring from the sample 7 are detected by the secondary charged particle detector 6 to detect and memorize an intensity of the secondary charged particles at a scan position. Based on distribution of the secondary charged particle intensity memorized, image data is created and displayed on the display CRT 10. At a time point that enough image data required for an architectural image is collected, the blanking electrode 3 is turned on to end the irradiation of the focused ion beam 30 to the sample 7.

In the case that the image displayed on the display CRT 10 deviates from a position to form and observe a section, the sample stage 8 is actuated to bring the predetermined position of the sample 7 to an appropriate position for display. At this time, the sample 7 may be moved with the beam blanking electrode 3 turned off while performing image display. Also, the sample stage 8 may be moved based on a result of calculation of a moving distance due to a difference from a target position determined from the image display. After the sample 7 is moved to an appropriate position for section formation and observation, an image is re-taken and displayed on the display CRT 10.

Figure 4:
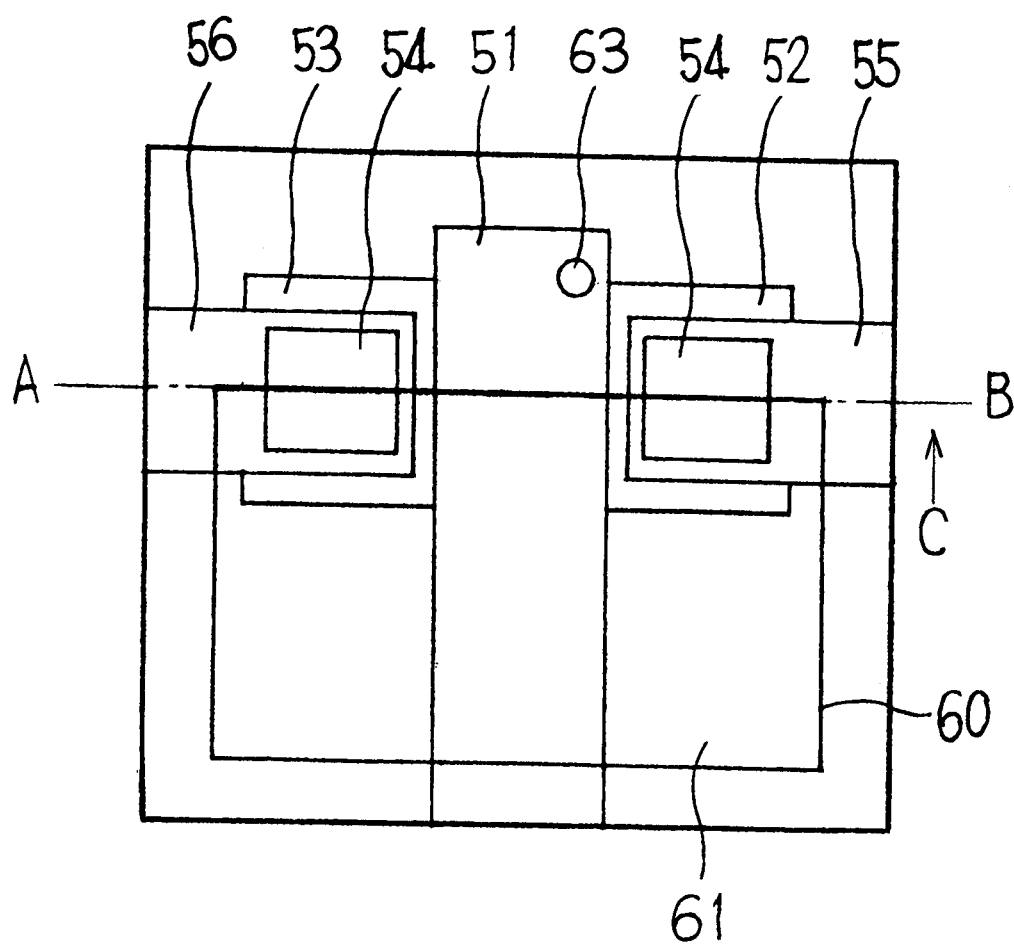
FIG. 4 is a plan view showing a forming method of the present invention.

Next, from the image displayed on the display CRT 10 as in FIG. 4, a work frame 60 is set which is of a rectangular region having as one side a section observing position (broken line A–B) on the sample 7. A focused ion beam 30 is repeatedly scanned over and irradiated to this work frame 60 region. By sputtering due to irradiation of the focused ion beam 30, a work region 60 as a scanned region is etched and formed into a recess 61. The recess 61 has a bottom at which the substrate 50 is exposed. At this time, as was explained in the previous section, a gate interconnect 51 on the D side becomes a conducting layer electrically floating.

Figure 2A:
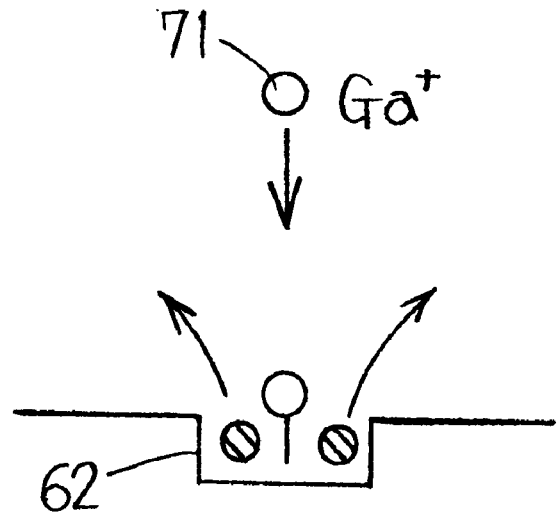
FIGS. 2A–2C are sectional views showing a situation of ion sputter.
Figure 2B:
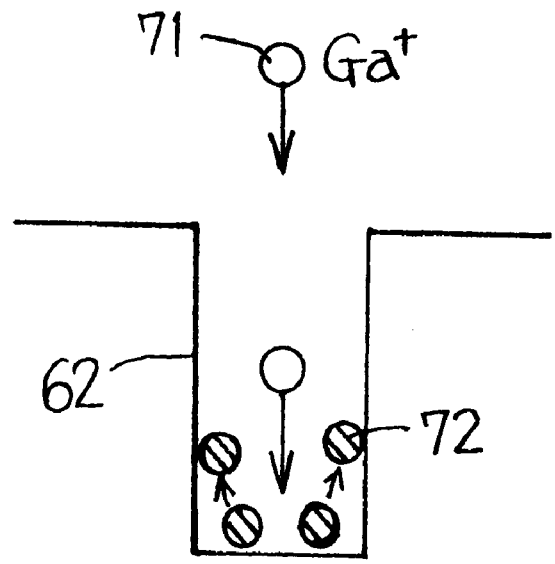
Figure 2C:
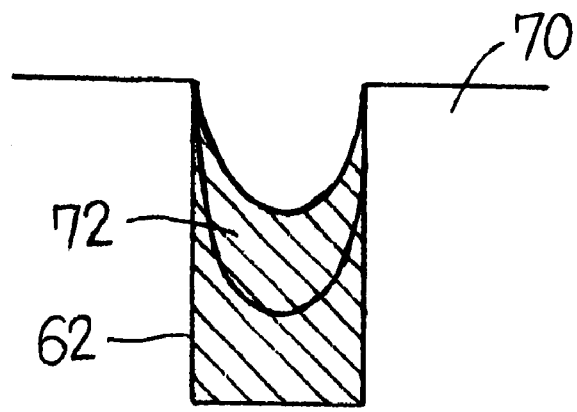

Subsequently, a focused ion beam without scanning is irradiated for a constant time to a point (second work region 63) at other than the work frame 60 but extremely close to the gate interconnect 51 rendered in a floating state due to the former recess formation step. Then a hole 62 is formed reaching the substrate 50. The second work region 63 is a spot to which a focused ion beam is irradiated for a constant time without scanning. Also, the region may be formed by the above hole with a depth greater than a greatest diameter of the above hole due to scanning and irradiating a focused ion beam over a very narrow region for a constant time. A second work region 63 is preferably a spot selected from a view point of minimum working time. The second region 63 is on the gate interconnect 51 rendered in an electrically floating state. Usually, although the sample 7 is formed with a protection film, it is natural in this case that the hole 62 and the recess 61 are formed including the protection film. The hole 62 thus formed is deposited at its sidewall with re-deposited materials 72 as shown in FIGS. 2B and 2C, and electrical conduction is available between first and second conductive layers at the upper and lower portions. That is, the gate interconnect 51 is free from charge-up.

Next, the sample 7 is inclined at an appropriate angle using a tilt function of the sample stage 8. The section to be observed is positioned upward with the section taken as a rotation axis. The section is scanned and irradiated by the focused ion beam in the afore-said method. Image data required for image formation is taken, and displayed on the display CRT 10 and memorized in an image data memory unit.

At this time, a substrate 50 of the sample 7 is electrically connected to the sample stage 8 and the sample stage 8 is grounded. Due to this, the electric charge irradiated to the section is discharged without charging.

Also, although one point irradiation of the focused ion beam 30 was performed after forming the section, it may be carried out before the section formation. Also, the irradiation is made without scanning, but irradiation with scanning may be applied provided that it is sufficiently narrow region for achieving the object.

Furthermore, although the focused ion beam was used for section observation, a different scanning electronic microscope is applicable. Also, it is possible to use a scanning electron microscope mounted on the focused ion beam in a complex form.

According to a method of the present invention, it becomes possible to observe a floating conductive region of a sample such as a semiconductor integrated circuit without charge-up phenomenon.

What is claimed is:

1. A method of forming a cross-section and observing the cross-section in a sample having a first conductive layer overlying a second conductive layer with an insulating layer interposed therebetween, comprising:

a first process of irradiating a focused ion beam and repeatedly scanning the focused ion beam across a predetermined region of the sample to form a recess having a sidewall in which at least the first conductive layer and the second conductive layer are exposed and the first conductive layer is rendered in an electrically floating state;

a second process of irradiating the focused ion beam at a region of the sample other than the predetermined region from above the first conductive layer rendered in an electrically floating state by, the first process to provide a hole extending from the first conductive layer to the second conductive layer and to electrically connect the firs conductive layer and the second conductive layer to prevent buildup of charge; and a third process of observing a desired exposed portion of the sample in the recess using a charged particle beam.

2. A method according to claim 1; wherein the second process comprises the step of irradiating a spot on the sample with the focused ion beam for a predetermined time without scanning the beam across the sample surface.

3. A method according to claim 1; wherein the second process comprises the steps of irradiating the focused ion beam onto the sample, and scanning the beam across a narrow region of the sample smaller than the predetermined region to form the hole with a depth deeper than a broadest diameter of the hole.

4. A method of forming a cross-section and observing the cross-section in a sample having a first conductive layer and a second conductive layer formed on the first conductive layer with an insulating layer interposed therebetween, comprising:

a first process of irradiating a focused ion beam onto the sample to form a hole in the sample extending from the first conductive layer to the second conductive layer and electrically connecting first conductive layer and the second conductive layer to prevent the buildup of charge;

a second process of forming a recess in the sample by irradiating the sample with a focused ion beam and repeatedly scanning the focused ion beam across a predetermined region of the sample in order to form a section for observation at a location different from a location of the hole; and a third process of observing a desired exposed portion of the sample in the recess formed in the second process using a charged particle beam.

5. A method according to claim 4; wherein the second process comprises the step of irradiating a spot on the sample with the focused ion beam for a predetermined time without scanning the beam across the sample surface.

6. A method according to claim 4; wherein the second process comprises the steps of irradiating the focused ion beam onto the sample, and scanning the beam across a narrow region of the sample smaller than the predetermined region to form the hole with a depth deeper than a broadest diameter of the hole.

7. A method according to claim 1; wherein the second process is performed so that a conductive substance of at least one of the first and second conductive layers is etched by the focused ion beam and re-deposited into the hole formed by the focused ion beam so as to electrically connect the first conductive layer and the second conductive layer.

8. A method according to claim 4; wherein the first process is performed so that a conductive substance of at least one of the first and second conductive layers is etched by the focused ion beam and re-deposited into the hole so as to electrically connect the first conductive layer and the second conductive layer.

9. In a method of performing cross-sectional analysis of a sample having stacked conductive layers separated by an insulating layer, the steps of:

forming a recess at a predetermined region of the sample using a focused ion beam to expose first and second conductive layers so that at least one of the conductive layers is rendered in an electrically floating state; and forming a hole in the sample extending from the first conductive layer to the second conductive layer at a region other than the predetermined region using the focused ion beam such that conductive material etched by the focused ion beam is re-deposited onto a surface of the hole to electrically connect the first and second conductive layers to prevent the buildup of charge.

10. A method of performing cross-sectional analysis of a sample according to claim 9; further comprising the step of observing a desired exposed portion of the sample in the recess using a charged particle beam.

11. A method of performing cross-sectional analysis of a sample according to claim 9; wherein the step of forming a hole in the sample comprises the step of irradiating a spot on the sample with the focused ion beam for a predetermined time without scanning the beam across the sample surface.

12. A method of performing cross-sectional analysis of a sample according to claim 9; wherein the step of forming a hole in the sample comprises the steps of irradiating the focused ion beam onto the sample, and scanning the beam across a narrow region of the sample smaller than the predetermined region to form the hole with a depth deeper than a broadest diameter of the hole.

13. A method of performing cross-sectional analysis of a sample according to claim 9; wherein the step of forming the recess is performed before the step of forming the hole.

14. A method of performing cross-sectional analysis of a sample according to claim 9; wherein the step of forming the hole is performed before the step of forming the recess.

15. A method of performing cross-sectional analysis of a sample having stacked conductive layers-separated by an insulating layer, comprising the steps of:

forming a recess at a predetermined region of the sample using a focused ion beam to expose first and second conductive layers so that at least one of the conductive layers is rendered in an electrically floating state to prevent the buildup of charge;

forming a conductive film for electrically connecting the first conductive layer and the second conductive layer; and observing a desired exposed portion of the sample in the recess using a charged particle beam.

16. A method of performing cross-sectional analysis of a sample according to claim 15; wherein the step of forming a conductive film for electrically connecting the first conductive layer and the second conductive layer comprises the step of forming a hole in the sample extending from the first conductive layer to the second conductive layer at a region of the sample other than the predetermined region using the focused ion beam such that conductive material etched by the focused ion beam is re-deposited onto a surface of the hole to electrically connect the first and second conductive layers.

17. A method of performing cross-sectional analysis of a sample according to claim 16; wherein the step of forming a hole in the sample comprises the step of irradiating a spot on the sample with the focused ion beam for a predetermined time without scanning the beam across the sample surface.

18. A method of performing cross-sectional analysis of a sample according to claim 16; wherein the step of forming a hole in the sample comprises the steps of irradiating the focused ion beam onto the sample, and scanning the beam across a narrow region of the sample smaller than the predetermined region to form the hole with a depth deeper than a broadest diameter of the hole.

19. A method of performing cross-sectional analysis of a sample according to claim 16; wherein the step of forming the recess is performed before the step of forming the hole.

20. A method of performing cross-sectional analysis of a sample according to claim 16; wherein the step of forming the hole is performed before the step of forming the recess.

* * * * *